United States Patent [19]
Lansdorp et al.

[11] Patent Number: 5,514,340
[45] Date of Patent: May 7, 1996

[54] DEVICE FOR SEPARATING MAGNETICALLY LABELLED CELLS

[75] Inventors: Peter Lansdorp; Terry Thomas, both of Vancouver, Canada

[73] Assignee: Magnetix Biotechnology, Inc., Vancouver, Canada

[21] Appl. No.: 185,064

[22] Filed: Jan. 24, 1994

[51] Int. Cl.$^6$ ................................................. B07C 5/344
[52] U.S. Cl. ...................... 422/101; 210/222; 210/695; 209/223.1; 209/223.2; 209/636; 422/99; 435/2; 435/7.23; 436/526
[58] Field of Search .................. 422/101, 99; 435/2, 435/7.23; 210/222, 695; 209/636, 223.1, 223.2; 436/526

[56] References Cited

U.S. PATENT DOCUMENTS

| | | | |
|---|---|---|---|
| 2,959,287 | 11/1960 | Davis et al. | 210/222 |
| 3,136,720 | 5/1964 | Baermann | 210/222 |
| 3,869,390 | 3/1975 | Heitmann et al. | 210/222 |
| 4,025,432 | 5/1977 | Nolan et al. | 210/222 |
| 4,190,524 | 2/1980 | Watson | 210/222 |
| 4,209,394 | 6/1980 | Kelland | 210/695 |
| 4,211,658 | 7/1980 | McDonald et al. | |
| 4,452,773 | 6/1984 | Molday | |
| 4,460,463 | 7/1984 | Yoshida | 210/695 |
| 4,505,824 | 3/1985 | Akamine et al. | 210/695 |
| 4,544,482 | 10/1985 | Rupp | 210/222 |
| 4,737,294 | 4/1988 | Kukuck | 210/695 |
| 4,868,109 | 9/1989 | Lansdorp | |
| 5,092,987 | 3/1992 | Schickel | 210/222 |

FOREIGN PATENT DOCUMENTS

WO90/07380 7/1990 WIPO.

OTHER PUBLICATIONS

Perry et al. Chemical Engineer's Handbook McGraw–Hill, N.Y. (1973) pp. 5–47 to 5–49.
Bieva et al., Exp. Hematol., 17:914–920, 1989.
Miltenyi et al., Cytometry, 11:231–238, 1990.
Kogler et al., Bone Marrow Transplant., 6:163–168, 1990.
Thomas et al., J. Hematother., 2:297–303, 1993.
Yau et al., Exp. Hematol., 18:219–222, 1990.
Poynton et al., The Lancet, Mar., p. 524, 1983.
Reading et al., Leukemia Res., 11(12):1067–1077, 1987.
Kato, K., and Radbruch, A., Cytometry, 14:384–392, 1993.
Molday, R. S. and Molday, L., FEBS. Lett. 170(2):232–238, 1984.
Kemshead, J. T., J. of Hematotherapy, 1:35–44, 1992 at pp. 36 to 39.

(List continued on next page.)

Primary Examiner—James C. Housel
Assistant Examiner—Jan M. Ludlow
Attorney, Agent, or Firm—Bereskin & Parr

[57] ABSTRACT

A device for separating magnetically labelled cells in a sample using an applied magnetic field having a housing; an inlet element at the top portion of the housing having an input end and an output end; a filter chamber adjacent to the output end of the inlet element for filtering the magnetically labelled cells from the fluid while allowing unlabelled cells to pass through when a magnetic field is applied thereto, and containing a multiplicity of magnetic matrix elements extending transversely across the filter chamber; and an outlet element for collecting the fluid which passes through the filter chamber having an input end coupled to the filter chamber and an output end. The device has one or more of the following features: (i) the inlet and/or outlet element having flow distribution means for distributing the flow from the inlet element generally uniformly across the filter chamber; (ii) the peripheries of the magnetic matrix elements are connected to the housing by a junction which is substantially impenetrable to the fluid; and (iii) the magnetic matrix elements are ordered and spaced apart so as to maximize the magnetic capture of magnetically labelled cells onto the magnetic matrix element when a magnetic field is applied. Methods of using the device and a hematopoietic cell preparation obtained using the device of the invention are also described.

21 Claims, 5 Drawing Sheets

OTHER PUBLICATIONS

Kemshead, J. T. The Immunomagnetic Manipulation of Bone Marrow in Bone Marrow Processing and Purging, 293, Gee, A. P. Ed., C.R.C. Press, Inc., Boca Raton, Florida, 1991.

Lansdorp et al., J. Exp. Med., 178:787–791, 1993.

Rebel et al., Blood, 83(1):128–136, 1994.

Ziolo et al., Science 257:219–223, 1992.

Molday, R. S. and MacKenzie, D., J. Immunol. Methods 52:353–367, 1982.

Staerz & Bevan, PNAS (USA) 83:1453–1457, 1986.

Staerz & Bevan, Immunology Today, 7(7&8):241–245, 1986.

Staerz et al., Nature, 314:628–631, 1985.

Perez et al., Nature 316:354–356, 1985.

Hoffmann, R. A. et al., Proc. Natl. Acad. Sci. U.S.A. 77(8):4914–4917, 1980.

Caldwell, C. W. and Taylor, H. M. Am. J. Clin. Path. 86:600, 1986.

Wognum et al., Cytometry 8:366–371, 1987.

Spangrude and Scollay, Exp. Hematol. 18:920–926, 1990.

Patent Abstracts of Japan, 23 Feb. 1988, vol. 12, No. 59(C–478)[2906] Diado Steel Co. Ltd, Multi–Flow Velocity Magnetic Filter, JP–A–62 204819, Sep. 1987.

FIG.1

| | TYPE OF FILTER | PERCENT DEPLETION CD8+ CELLS |
|---|---|---|
|  | 23 LAYERS MAGNETIC SCREEN NO SPACERS | 90% |
|  | 10 LAYERS MAGNETIC SCREEN AND SPACERS | 96% |
|  | 3 LAYERS AND SPACERS AT TOP OF CHAMBER | 59% |
|  | 3 LAYERS - TOP, MIDDLE, BOTTOM | 80% |
|  | KNIT MESH 50μm LAYERED WITH SUPPORT | 72% |

NO BEADS

FIG.4A

8/10 MESH

FIG.4B

12/14 MESH

FIG.4C

12/16 MESH

FIG.4D

16/20 MESH

FIG.4E

20/30 MESH

DEVICE FOR SEPARATING MAGNETICALLY LABELLED CELLS

FIELD OF THE INVENTION

The present invention relates to a device for separating magnetically labelled cells in a sample using an applied magnetic field, and methods of using the device to prepare purified cell preparations, preferably hematopoietic stem cell preparations depleted of selected cells such as T lymphocytes, tumor cells and/or red blood cells. The invention also relates to purified hematopoietic stem cell preparations.

BACKGROUND OF THE INVENTION

Blood cells have a relatively short life span and need to be replenished throughout life. In adults, blood cell formation or hematopoiesis takes place in the bone marrow, but blood-forming stem cells can also be found in peripheral blood. Hematopoietic cells represent a hierarchy of proliferating and differentiating cells. The most abundant are the differentiating cells. These cells have limited or no proliferative capacity and represent the immediate precursors of the specialized end cells that are found in blood. The immediate precursors of the differentiating cells are the progenitor cells. Most of these cells are restricted to differentiate along a single lineage but they may have quite extensive proliferative capacity. Progenitor cells appear morphologically as blast cells and they typically do not have specific features of the hematopoietic lineage to which they are committed. Progenitor cells are derived from stem cells. Stem cells have been historically defined by their ability to self-renew as well as to generate daughter cells of any of the hematopoietic lineages. The presence of stem and progenitor cells may be detected by their ability to produce colony-forming cells in culture. They may also be detected by screening for the CD34 antigen which is a positive marker for early hematopoietic cells including colony forming cells and stem cells.

There is a continued interest in developing stem cell purification techniques. Pure populations of stem cells will facilitate studies of hematopoiesis. Transplantation of hematopoietic cells from peripheral blood and/or bone marrow is also increasingly used in combination with high-dose chemo- and/or radiotherapy for the treatment of a variety of disorders including malignant, non-malignant and genetic disorders. Very few cells in such transplants are capable of long-term hematopoietic reconstitution and thus there is a strong stimulus to develop techniques for purification of hematopoietic stem cells. Furthermore, serious complications and indeed the success of a transplant procedure is to a large degree dependent on the effectiveness of the procedures that are used for the removal of cells in the transplant that pose a risk to the transplant recipient. Such cells include T lymphocytes that are responsible for graft versus host disease (GVHD) in allogeneic grafts and tumour cells in autologous transplants that may cause recurrence of the malignant growth.

A variety of techniques have been described for the removal of either T cells or tumour cells from transplants (See for example Bone Marrow Processing and Purging: A Practical Guide, (ed. A. P. Gee), CRC Press, Boca Raton (1991)). Most of the techniques involve purification of the hematopoietic cells ("positive selection") or the depletion or "purging" of tumour cells ("negative selection") in the cell preparation used for transplantation.

The two most important variables in either positive or negative selection techniques are (1) the efficiency of removal of undesirable cells (either T cells or tumor cells) and (2) the recovery of hematopoietic cells (most readily assessed by measurement of CD34 positive cells before and after the separation). These variables are typically expressed as (1) the logarithm (log) of the depletion and (2) the percentage recovery of the CD34 positive cells. For example, a technique for depleting T cells in a cell suspension that results in a two log depletion of T cells, and a 30% recovery of CD34 positive cells, would provide a cell suspension containing 1% of the T cells and 30% of CD34 positive cells that were present in the cell suspension before the T cell depletion procedure.

High gradient magnetic separation (HGMS) has been used for the removal of magnetically labelled cells from suspensions of bone marrow cells for research use (Bieva et al., Exp. Hematol. (1989) 17: 914; Miltenyi et al., Cytometry (1990) 11: 231; and Kogler et al., Bone Marrow Transplant. (1990) 6: 163 and Thomas et al., J. Hematother. (1993) 2: 297; and clinical use (Yau et al., Exp. Hematol. (1990) 18: 219; Poynton et al., The Lancet (1983) March: 524; and Reading et al., Leukemia Res. (1987) 11: 1067).

HGMS separation involves placing a filter of fine magnetisable wires in a strong magnetic field. High gradient magnetic fields are produced around the wires, allowing the capture of even very weakly magnetic particles upon the magnetisable wires.

There have been several attempts to apply HGMS to the separation and isolation of magnetically labelled CD34 positive cells (i.e. positive selection techniques), although the recoveries and purities achieved have been undesirably low (For example, see Kato, K., and Radbruch, A., Cytometry 14:384, 1993). Typically, attempts have employed an HGMS filter which consists of a random or semi-random array of stainless steel wire wound loosely into a column located in a strong magnetic field (Miltenyi, S. et al., Cytometry 11:231, 1990; Molday, R. S. and Molday, L., FEBS. Lett. 170:232, 1984; Kato, K and Radbruch, A., supra; Kemshead, J. T. in Hematotherapy 1:35, 1992; and Kemshead, J. T. in Bone Marrow Processing and Purging, 293, Gee, A. P. Ed., C. R. C. Press, Inc., Boca Raton, Fla., 1991). The positive selection procedures suffer from many disadvantages including the presence of materials such as antibodies and/or magnetic beads on the CD34 positive cells, and damage to the cells resulting from the removal of these materials.

It has been assumed that pure hematopoietic stem cells can be numerically expanded in the laboratory. Accordingly, investigators typically have not focused on the recovery or yield of hematopoietic stem cells that can be obtained with the available cell purification or cell "purging" methods. However, recent studies with highly purified candidate stem cells from human and murine bone marrow have shown that it may not be possible to achieve such numerical expansion of stem cells derived from adult hematopoietic tissue in vitro (Lansdorp et al., J. Exp. Med. (1993) 178: 787, and Rebel et al., Blood (1994) 83:128). As a result, techniques that optimize the use of the available hematopoietic cells for transplantation are of considerable interest. Unfortunately, all currently available methods for the removal of either T cells or tumour cells from transplants suffer from deficiencies. These include the following: 1) the methods that allow for effective (i.e. >2 log) depletion of T or tumour cells typically recover generally far less than 50% of the normal blood-forming or hematopoietic cells initially present in the cell suspension available for transplantation (i.e. as a result of centrifugation, density separation, wash procedures and other preprocessing required prior to the actual separation process or during the immunological selection procedure itself); and/or 2) the methods that recover >50% of the hematopoietic cells fail to reproducibly achieve effective (>2 log) depletion of undesirable cells.

SUMMARY OF THE INVENTION

The present inventors have developed a device for removing magnetically labelled cells from a sample containing magnetically labelled cells and non-magnetically labelled cells, without significant loss of non-magnetically labelled cells present in the sample. The separation of weakly magnetic cells by HGMS from non-magnetic cells, without significant loss of the non-magnetic cells was found by the present inventors to be dependent on the following variables: (1) magnetic forces that attract magnetically labelled cells to the magnetized wires; (2) fluid shear forces acting on all cells in the solution; (3) non-specific entrapment of non-magnetic cells; and (4) contact between magnetic cells and the magnetic matrix. Hitherto no one else has described a single device that addresses all of these important variables. However, the four variables are controlled in an embodiment of the device of the present invention in that the device has a) an ordered magnetic HGMS matrix with a design that incorporates spacing of the magnetic wires to increase HGMS efficiency; (b) a flow distributor that ensures an even fluid flow around all magnetic wires; and (c) a filter design that ensures close approximation of magnetic cells to the magnetized wires of the magnetic matrix and yet does not entrap many non-magnetic cells.

The present inventors have shown that the use of magnetic wires in an ordered array in the device of the present invention offers many advantages over a random packing of wires. The use of alternating layers of magnetic and non-magnetic mesh also has been found to ensure optimal spacing of the magnetizable wires, minimal entrapment of non-magnetic cells as well as a rigid architecture of the device that enhances reproducibility of construction and behaviour.

The present inventors have also found that the random distribution of flow around all magnetized wires could be maximized using a flow distributor. The present inventors prepared a simple and effective flow distributor by inserting particles, preferably rigid spherical particles ranging in size between 50 μm to 1000 μm in diameter, in the inlet and outlet of the device. While the use of spherical flow distributor beads or particles is preferred as the flow distribution means, any suitable arrangements which produces a uniform flow through the filter chamber may be used. For example, effective and even expansion and contraction of fluid flow containing suspended cells may also be achieved using carefully designed inserts containing vertical and horizontal flow dividers and openings. The angle of flow expansion/contraction could also be decreased by elongation of the filter inlet and outlet.

Further, the present inventors have found that connecting the peripheries of the magnetic meshes to the housing prevented flow around the meshes and increased the retention of magnetically labelled cells allowing for increased purity of non-magnetically labelled materials. The peripheries of the magnetic meshes may be connected to the housing by encasing the stack of meshes in heat-shrink tubing, a moulded plastic housing or, by precise mechanical matching of magnetic mesh and filter housing at a tolerance of 0.2 mm or less.

The device and methods described herein are preferably used to deplete T lymphocytes and tumor cells from samples to prepare hematopoietic cell preparations for use as transplants as well as other therapeutic methods. Removal of the T lymphocytes from an allogeneic transplant is an effective way to prevent Graft Versus Host Disease (GvHD) which is the major problem in patients receiving allogeneic bone marrow transplants (Champlin, R. J., Hematother. 2:27–42, 1993). Cell dose in the transplant has also been shown in model studies in rats to be a critical factor in prevention of graft rejection (Uharek et al., Blood 79:1612–1621, 1992). Accordingly, the goal of T cell depletion techniques is to effectively deplete T cells without significant losses of the hematopoietic cells that express CD34. Methods that effectively (>2 log) deplete T cells and recover a high proportion (>50%) of the $CD34^+$ cells are highly desirable. In contrast to hitherto known techniques, the device of the present invention allows such a cell population to be obtained without using multi-step procedures which are laborious and time-consuming. The cell preparations that can be obtained with the methods of the present invention, represent a significant advance in the art of bone marrow transplantation. The methods of the present invention are fast (less than two hours), require minimal processing of the sample and yet deplete CD3+ T cells at a good efficiency (>2 log depletion) while recovering >50% of $CD34^+$ cells.

Accordingly, broadly stated the present invention relates to a device for removing magnetically labelled cells from a sample using an applied magnetic field, comprising:

(a) a housing;

(b) an inlet element at the top portion of the housing having an input end and an output end;

(c) a filter chamber adjacent to the output end of the inlet element for filtering the magnetically labelled cells from the fluid while allowing unlabelled cells to pass through when a magnetic field is applied thereto, and containing a multiplicity of magnetic matrix elements extending transversely across the filter chamber;

(d) an outlet element for collecting the fluid which passes through the filter chamber having an input end coupled to the filter chamber and an output end;

and which device has one or more of the following features:

(i) the inlet and/or outlet elements having flow distribution means comprising spherical particles for distributing the flow generally uniformly across the filter chamber;

(ii) the peripheries of the magnetic matrix elements are connected to the housing by a junction which is substantially impenetrable to the fluid, and which is created by a heat shrink material, which forms the housing and secures the inlet and outlet elements in position; and (iii) the magnetic matrix elements are ordered and spaced apart so as to maximize the magnetic capture of magnetically labelled cells onto the magnetic matrix when a magnetic field is applied.

The present invention also broadly contemplates a method of using the device of the invention to deplete selected cells from a sample. Accordingly, in a preferred embodiment the invention provides a method of using the device to deplete selected cells, preferably T lymphocytes, tumor cells, or red blood cells from a sample, preferably blood or bone marrow comprising:

a) magnetically labelling the selected cells to obtain magnetically labelled cells;

(b) passing the sample containing the magnetically labelled cells through a device as described above in the presence of a magnetic field;

c) collecting a preparation which is substantially depleted of the magnetically labelled cells.

The present invention still further contemplates a hematopoietic cell preparation comprising hematopoietic cells and which is characterized as follows:

a) it is obtained by high gradient magnetic cell separation from a sample which contains hematopoietic cells and T lymphocytes or tumor cells;

b) it contains greater than 50% of the hematopoietic cells present in the sample; and c) T lymphocytes or tumour cells in the sample are depleted by greater than 2 logarithms.

These and other aspects of the present invention will become evident upon reference to the following detailed description and attached drawings. In addition, reference is made herein to various publications, which are hereby incorporated by reference in their entirety.

BRIEF DESCRIPTION OF THE DRAWINGS

The invention will now be described with reference to the accompanying drawings, in which.

DETAILED DESCRIPTION OF THE INVENTION

I. Description of a Preferred Device of the Invention

Figure 1:
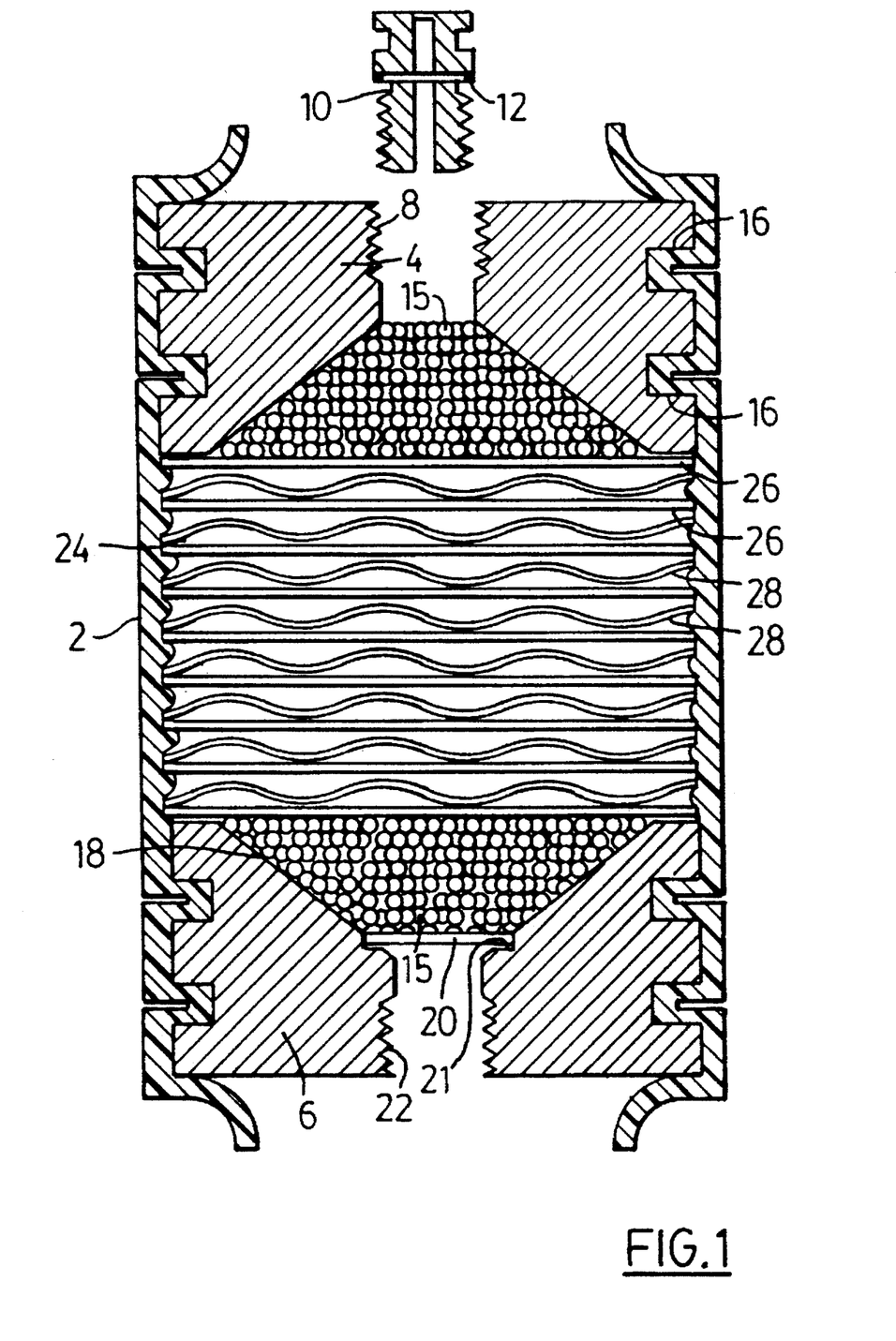
FIG. 1 is a cross-sectional view of a device including a filter according to the present invention.

The device of the invention will now be described with reference to the Figures. In FIG. 1, the whole device is denoted by the reference 1, and incorporates a housing 2. The material for the housing can be selected depending on the application. Suitable materials include tubular forms of non-magnetic metals or synthetic polymers, such as regular or heat-shrinkable plastics. For clinical applications, medical grade tubing, which is relatively puncture-proof should be used. In a preferred embodiment, the housing 2 is formed from tubular material for example, heat shrinkable material, as detailed below.

Within the housing 2, there is an inlet element 4 and an outlet element 6. The inlet element 4 has a threaded inlet port 8. A connector 10 includes an O ring 12, and is adapted to engage the threaded inlet port 8. In known manner, the connector 10 provides a Luerlock connector for connection to tubing.

The inlet element 4 defines a flow distribution chamber 14, which is generally frusto-conical. The chamber 14 extends from an input end of relatively small diameter to an output end having a larger diameter cone angle between 135° and 90°. Within the chamber 14, there are a plurality of spherical particles 15 which are preferably rigid or semi-rigid, for example, glass beads, and polyacrylamide beads, that cause flow through the input end to be evenly distributed across the lower, output end of the chamber 14. The spherical particles are generally 50 µm to 1000 µm in diameter, preferably spherical particles of 700–1000 µm in diameter are used.

In this embodiment, at the outside of the inlet element 4, there are two annular grooves 16, to ensure positive engagement with the housing 2, again as detailed below.

It is anticipated that, for large scale production, the housing 2 would be moulded in plastic, in which case a variety of connection arrangements could be employed between the housing 2 and the inlet and outlet elements 4,6.

The outlet element 6 generally corresponds to the inlet element 4. It defines a frusto-conical chamber 18, and also has annular grooves 16. The frusto-conical chamber 18 has at its top a first input end of relatively large diameter, and at its bottom a second output end of relatively small diameter. Again, within the chamber 18 there are spherical particles 15 such as glass beads, intended to ensure that the flow into the chamber 18 is uniformly distributed across the inlet end. To support the spherical particles 15, there is an output mesh support 20, engaged in an annular step 21 at the outlet element 6. Since flow is downwards through the device 1, no such mesh support is required in the inlet chamber 14.

The outlet element 6 has a threaded port 22, for connection to a Luerlock connector and tubing, as for the port 8 at the inlet.

Between the inlet and outlet elements 4, 6, there is defined a filter chamber 24. Within this filter chamber 24, layers of magnetic mesh 26 are alternately vertically spaced with layers of non-magnetic mesh 28. As shown, there are nine layers of magnetic mesh and eight layers of non-magnetic mesh.

The layers of magnetic mesh 26 are generally planar. Each layer comprises, in known manner, magnetic wires extending in generally perpendicular directions and interwoven. The topmost magnetic layer 26 defines the bottom of the inlet chamber 14 and serves to retain the spherical particles 15 in position. Similarly, the lowermost magnetic mesh 26 defines the top of the outlet chamber 18. Further, although the spherical particles 15 will naturally be retained in the outer chamber 18 by gravity and downward flow of any fluid, this layer of mesh 26 also serves to retain these spherical particles 15 in position.

Figure 2:
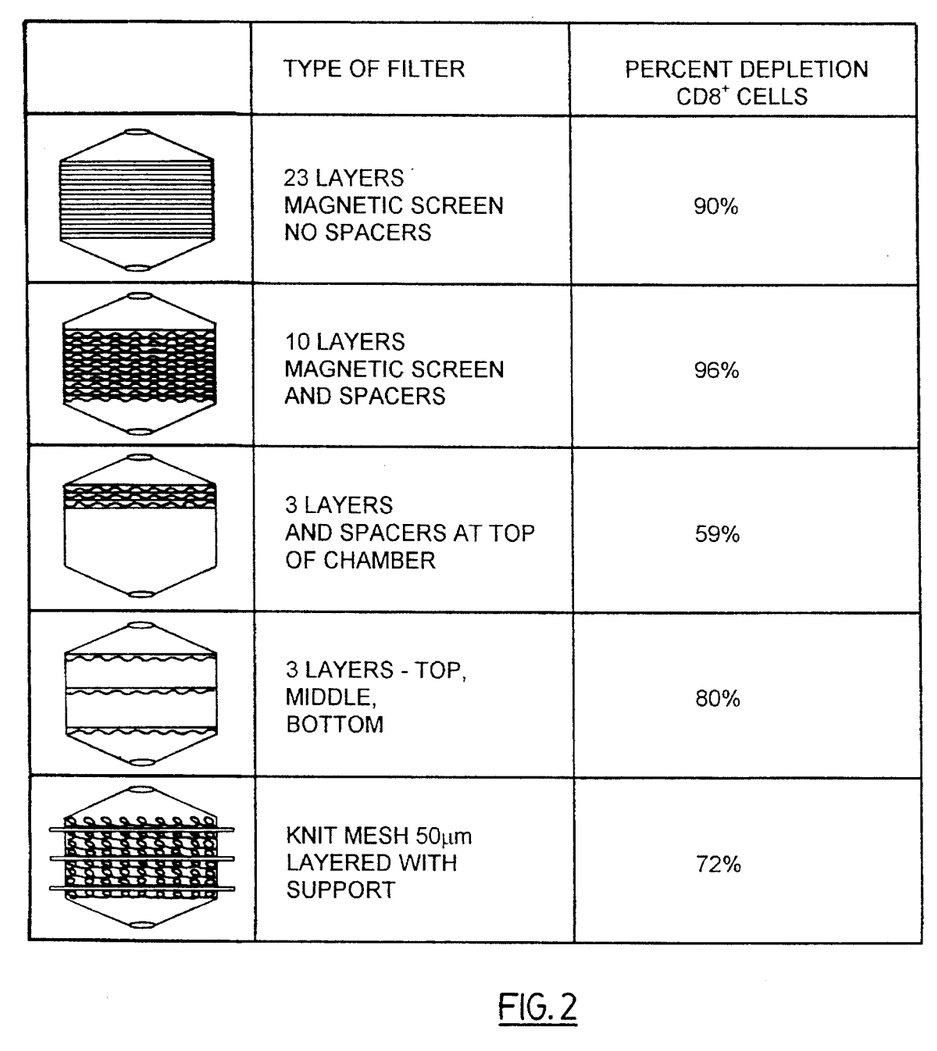
FIG. 2 is a schematic chart, comparing different filter materials and their spacing.

The non-magnetic mesh layers 28 are made of interwoven wires with a threefold larger diameter than the wires in the magnetic mesh layers 26 to provide desired spacing between magnetic mesh layers 26. As such, the layers 28 should be dimensioned so as to provide a spacing between the magnetic mesh layers 26 of approximately 6 to 9 times the diameter of the magnetic wires of the magnetic meshes 26. The number of magnetic layers depends on the separation requirements and can vary from 5 to 100. Where the device is used to deplete T lymphocytes and/or tumor cells from a sample, 40 to 60 layers are generally required to obtain a greater than 3 log depletion, and about 10 layers are generally required to obtain a 1 to 2 log depletion. FIG. 2 is a schematic diagram indicating the effect of spacing of the magnetic matrix elements or screens on the separation efficiency. As shown at the top, with 23 layers of magnetic screens, with no spaces, the percentage depletion for $CD8^+$ cells is 90%. The most efficient separation, 96%, is obtained with ten layers (note 9 in FIG. 1) of magnetic screens and spacers. The lowest separation efficiency was obtained (59%) when three layers of magnetic screens are used with spacers located at the top of the filter chamber 24, i.e.

adjacent the inlet. With the three magnetic screens spaced evenly in the top, middle and bottom of the filter chamber 24, an efficiency of 80% was achieved, indicating that spacing of the magnetic screens inside the filter chamber 24 is desirable. Finally, with knit mesh magnetic wires of 50 microns in diameter, which were not supported by non-magnetic screens but by non-magnetic wires that extend through the filter housing, an efficiency of 72% was achieved.

To assemble the device 1, the housing 2 is located vertically as shown in FIG. 1, but with the heat shrink material of the housing in an initially, unshrunk state, so that it has a diameter generally larger than the various elements within the housing 2, to permit these elements to be freely inserted and assembled. The housing 2 is initially purely cylindrical. The outlet element 6 is placed within the housing 2, the mesh 20 placed in position, and the spherical particles 15 evenly distributed on top of the mesh 20. The magnetic and non-magnetic meshes are then placed on top of the output element 6 alternately as shown. The input element 4 is then placed in position on the top most magnetic mesh 26, and the appropriate quantity of spherical particles 15 inserted through the threaded inlet port 8.

Then, it is ensured that the various elements are aligned and the input and output elements 4, 6 are pressed together to maintain the various elements in the desired alignment. The housing 2 is then subjected to sufficient temperature to cause it to shrink in known manner. As shown, this will cause the material of the housing 2 to engage the annular grooves 16 of the input and output elements 4, 6. Also, as shown, the peripheries of the meshes 26, 28 become embedded in the housing 2 without penetrating it, while supporting the housing 2, so as to provide a junction which is substantially impenetrable to fluid.

It will be appreciated that the spherical particles 15 may be inserted in chamber 14 before or after the housing is subjected to sufficient temperature to cause it to shrink, or just prior to use of device 1. The ends of the tubular housing 2 will extend radially inwardly, as shown in FIG. 1.

The device 1 is then fully assembled and ready for connection with the connectors 10 in known manner. The fully assembled device may be sterilized before use by conventional techniques such as autoclaving.

In use, a sample containing magnetically labelled cells is directed into device 1 at input element 4. The sample enters the flow distribution chamber 14 and passes through the plurality of spherical particles 15. The sample enters the filter chamber 24 and travels through the layers of magnetic mesh and non-magnetic mesh in the presence of a uniform strong magnetic field produced by a magnet, for example, a solenoid electromagnet. In the process, magnetised cells are retained on the magnetised magnetic mesh 26. The sample, including non-magnetic materials, passes through filter chamber 24 and into the outlet element 6. The sample enters the first input end of outlet element 6 and its flow is uniformly distributed by the plurality of spherical particles 15. Use of the filter device provides efficient separation of magnetically labelled cells.

II. Removal of Cells from a Sample

The device of the invention may be used to deplete selected cells from a sample, such as cells which express cell surface antigens recognized by antibodies, preferably monoclonal antibodies. In one embodiment of the invention the method is used to deplete selected cells from cell suspensions obtained from blood and bone marrow. In particular, the method may be used to deplete tumor cells from bone marrow or blood samples harvested for autologous transplantation, or deplete T lymphocytes from bone marrow or blood samples harvested for allogeneic transplantation. The device of the invention may also be used to remove virus particles from a sample.

The selected cells to be depleted in the sample may be magnetically labelled by conjugating the cells to magnetic particles. Suitable magnetic particles include particles in ferrofluids and other colloidal magnetic solutions. "Ferrofluid" refers to a colloidal solution containing particles consisting of a magnetic core, such as magnetite ($Fe_3O_4$) coated or embedded in material that prevents the crystals from interacting. Examples of such materials include proteins, such as ferritin, polysaccharides, such as dextrans, or synthetic polymers such as sulfonated polystyrene cross-linked with divinylbenzene. The core portion is generally too small to hold a permanent magnetic field. The ferrofluids become magnetized when placed in a magnetic field. Examples of ferrofluids and methods for preparing them are described by Kemshead J. T. in J. Hematotherapy, 1:35, 1992, at pages 36 to 39, and Ziolo et al. Science (1994) 257:219 which are incorporated herein by reference. Colloidal particles of dextran-iron complex (See Molday, R. S. and McEnzie, L. L. FEBS Lett. 170:232, 1984; Miltenyi et al., Cytometry 11:231, 1990; and Molday, R. S. and MacKenzie, D., J. Immunol. Methods 52:353, 1982; Thomas et al., J. Hematother. 2:297 (1993); and U.S. Pat. No. 4,452,733, which are each incorporated herein by reference) are preferably used in the method of the invention.

Substances which are capable of binding to the selected cells to be depleted such as lectins, carbohydrates, proteins, and antibodies specific to an antigen on the surface of the cells, preferably antibodies, may be chemically bound to the surface of the magnetic particles for example, using cyanogen bromide. When the magnetic particles are reacted with a sample containing the selected cells, conjugates will form between the selected cells and the magnetic particles with bound substances. The reaction conditions are suitable to allow the selected cells to bind to the magnetic particles to form conjugates.

Alternatively, the selected cells to be depleted may be magnetically labelled by indirectly conjugating the selected cells to the magnetic particles by means of antibody reagents. Examples of antibody reagents are bispecific antibodies, tetrameric antibody complexes, and biotinylated antibodies.

Bispecific antibodies may contain a variable region of an antibody, for example, murine antibody, specific for at least one antigen on the surface of the magnetic particles, and a variable region of a second antibody which is capable of binding to at least one antigen on the surface of the selected cells. The bispecific antibodies may be prepared by forming hybrid hybridomas. The hybrid hybridomas may be prepared using the procedures known in the art such as those disclosed in Staerz & Bevan, (1986, PNAS (USA) 83: 1453) and Staerz & Bevan, (1986, Immunology Today, 7:241). Bispecific antibodies may also be constructed by chemical means using procedures such as those described by Staerz et al., (1985, Nature, 314:628) and Perez et al., (1985 Nature 316:354), or by expression of recombinant immunoglobulin gene constructs.

A tetrameric immunological complex may be prepared by mixing a first monoclonal antibody which is capable of binding to at least one antigen on the surface of the magnetic particles and a second monoclonal antibody which is capable of binding to at least one antigen on the surface of the selected cells. The first and second antibody are from a first animal species. The first and second antibody are reacted with an about equimolar amount of monoclonal antibodies of a second animal species which are directed against the Fc-fragments of the antibodies of the first animal species. The first and second antibody may also be reacted with an about equimolar amount of the F(ab')$_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of methods for preparing tetrameric antibody complexes).

The use of biotinylated antibodies in combination with magnetic iron-dextran particles that are covalently labelled with (strept) avidin for the indirect magnetic labelling of selected cells recognized by monoclonal antibodies is described by Miltenyi, S. et al., Cytometry 11:231, 1990. Many alternative indirect ways to specifically cross-link colloidal magnetic particles to selected cells would also be apparent to those skilled in the art.

When the method of the invention is used to remove tumor cells from autologous blood or bone marrow grafts, antibodies specific for different cell surface antigens on the tumor cells may be conjugated to the magnetic particles or used in the antibody reagents. For example, for removal of lymphoma cells antibodies to cell surface antigens that are expressed on lymphoma cells such as CD10, CD19 and CD20 may be used. Monoclonal antibodies specific for epithelial antigens such as high molecular weight mucins may be used for the depletion of carcinoma cells. Where the method is used to deplete T lymphocytes from a sample, antibodies to cell surface antigens such as CD2, CD3, CD5, CD4, CD6, CD8 and CD28 may be used.

The sample containing the selected cells is reacted with the antibody reagents so that the selected cells present in the sample bind to the antibody reagents to form conjugates of the selected cells and the antibody reagents. The reaction conditions are selected to provide the desired level of binding of the selected cells and the antibody reagents. For depletion of cells targeted by antibody reagents, a sample containing the selected cells to be depleted and cells to be isolated is preferably incubated with antibody reagents for a period of 5 to 60 minutes at either 4° or ambient room temperature. The concentration of the antibody reagents is selected depending on the estimated concentration of the selected cells in the sample and the specificity of the antibodies of the antibody reagents. Generally, the concentration is between about 0.1 to 50 µg/ml of sample. The magnetic particles are then added and the mixture is incubated for a period of about 5 minutes to 30 minutes at the selected temperature. The sample is then ready to be separated over the device of the present invention.

The sample containing the magnetically labelled conjugates is passed through a device of the invention in the presence of a magnetic field using the procedures outlined in detail above. In an embodiment of the invention, the fluid flow, gravity and the external magnetic field are generally in the same direction and the magnetic matrix elements are perpendicular to this. The magnet is preferably a solenoid electromagnet with a 3" diameter bore and having a magnetic field of 0.5–2 Tesla.

The magnetically labelled conjugates are retained in the high gradient magnetic column and the materials which are not magnetically labelled flow through the column after washing with a buffer. The preparation containing non-magnetically labelled cells may be further analyzed using procedures such as flow cytometry.

III. Uses of the Device and Methods of the Invention

The device and methods of the invention may be used in the processing of biological samples including bone marrow, cord blood and whole blood.

The device and methods of the invention are preferably used to deplete or purge tumour cells or T lymphocytes from samples to prepare hematopoietic cell preparations for use in transplantation as well as other therapeutic methods that are readily apparent to those of skill in the art. For example, in the case of an autologous transplant, bone marrow can be harvested from a patient suffering from lymphoma or other malignancies, the sample may be substantially depleted of any tumor cells using the device and methods described herein, and the resulting hematopoietic cell preparation may be used in therapeutic methods. Bone marrow or blood can also be harvested from a donor in the case of an allogenic transplant and depleted of T lymphocytes by the methods described herein.

Using the method of the invention it is possible to recover a highly purified preparation of hematopoietic cells. In particular, a hematopoietic cell population containing greater than 50% of the hematopoietic cells present in the original sample, and which is depleted of T lymphocytes or tumour cells in the original sample by greater than 2 logarithms may be obtained. The hematopoietic cells in the preparation are not coated with antibodies or modified making them highly suitable for transplantation and other therapeutic uses that are readily apparent to those of skill in the art.

The method and device of the invention may also be used to remove red blood cells from samples such as blood and bone marrow. Half of the volume of normal blood consists of mature red blood cells. Typically these cells exceed nucleated cells by >100 fold. For many clinical and research applications, removal of red blood cells is required or desirable. The present invention provides more efficient procedures for removing red blood cells with higher recovery of cells than conventional methods such as Ficoll-Hypaque density centrifugation (See Example 7 herein).

In a particular application of the invention, samples may be processed using the methods and device described herein for diagnostic flow cytometry of leukocyte subpopulations. For example, the methods may be used to prepare blood samples of patients infected with the Human Immuno Deficiency (HIV) virus for monitoring lymphocyte populations in such patients. Enumeration of the absolute numbers of leukocyte subpopulation by conventional immunofluorescence measurements and flow cytometry has been complicated by the abundant presence of red blood cells in peripheral blood and consequently, such enumerations are most often derived from separate measurements of nucleated cells numbers and immunophenotype (Hoffmann, R. A. et al.Proc. Natl. Acad. Sci. U.S.A. 77: 4914, 1980.). A variety of procedures have been proposed and are used to remove red blood cells from blood for immunophenotypic measurements but these procedures are labour intensive and difficult to automate and in some cases the procedure itself may interfere with immunofluorescence measurements (Caldwell, C. W. and Taylor, H. M. Am. J. Clin. Path. 86: 600, 1986). In contrast, the present invention provides an efficient and direct method for removing red blood cells from blood samples that can readily be automated as no centrifugation or wash steps are involved.

The following non-limiting examples are illustrative of the present invention:

EXAMPLE 1

The Effects of Changes in the Construction of the Device On Cell Separation

The ability of a filter device with various constructions to separate T-cells from peripheral blood mononuclear cell suspensions was tested. The following materials and methods were used in the investigation:

Materials and Methods

Magnetic Colloidal Dextran Iron

The procedure for making dextran iron particles described by Molday and MacKenzie (Molday and MacKenzie, J. Immunol. Meth. (1982) 52: 353–368) was modified as follows. 1.51 g $FeCl_2.6H_2O$ and 0.64 g $FeCl_24H_2O$ were dissolved in 20 ml distilled water. This solution was heated to 60° C. and 10 g of Dextran T-40 (Pharmacia, Uppsala, Sweden) was added. The mixture was stirred continuously and the dextran iron dissolved (temperature can be increased to 80° C. if necessary). Aqueous ammonium (25%) was added to the solution dropwise to titrate the pH to 10. The first two mls were added very slowly and approximately 15 ml total was required. After the pH was set at 10 the mixture was heated to 75°–80° C. for 15 min. with continuous stirring. The resulting colloidal suspension was cooled to room temperature and centrifuged at 1,000 g for 5 min. to remove aggregates. The supernatant was filtered first through a course Watman filter and then a 0.2μmembrane filter. The non-magnetic iron and free dextran were removed from the magnetic colloidal particles using High Gradient Magnetic Separation (see filter construction and separation conditions below). The dextran-iron suspension was passed through a 1.5 inch diameter 40 layer HGMS filter as described herein in a 0.5 Tesla magnetic field (solenoid magnet) at 2.5 cm/min. The filter was washed with 200 ml of water and 300 ml phosphate buffered saline pH 7.4 (PBS). The magnetic field was then reduced to zero and the magnetic particles collected by washing the filter with 100 ml of PBS. The suspension of magnetic particles was filtered (0.2μfilter), placed in a sterile tube and the optical density (1 cm) at 450 nanometer ($OD_{450}$) recorded. Within 48 hours of use, the magnetic colloidal particles were separated again using the same HGMS procedure without the 200 ml water wash.

Antibodies

The mouse $IgG_1$ anti-human CD3 monoclonal antibody (UCHT1) was provided by Dr. P. Beverley, ICRF, London and is described by Beverley and Callard (Beverley and Callard, Eur. J. Immunol., (1981) 11: 329–334). The mouse $IgG_1$ anti-human CD8 monoclonal antibody OKT5 (Basch, In: Leucocyte Typing, eds. Bernard, Boumsell, Dausset, Milstein, Schlossman (1984) pp. 661–664) was purified from culture supernatants of the OKT5 hybridoma line obtained from American Tissue Culture Collection (ATCC). The mouse $IgG_1$ anti-dextran monoclonal antibody (DX1) was purified from culture supernatants produced by a switch variant of the hybridoma 341G6 as previously described (Thomas et al., J. Immunol. Meth. (1992), 154: 245–252). F(ab')a fragments of the rat monoclonal $IgG_1$ antibody TFL-P9 specific for the Fc portion of the mouse $IgG_1$ molecule were obtained by pepsin digestion of purified immunoglobulin as described previously (Thomas et al., J. Immunol. Meth. (1989), 120: 221–231). Tetramolecular antibody complexes (U.S. Pat. No. 4,868,109) were prepared by mixing the OKT5 or UCHT1 antibody with the anti-dextran antibody (DX1) and then adding the $F(ab')_2$ rat anti-mouse $IgG_1$ antibody in a molar ratio of 1:4:5 respectively for OKT5, and 1:2:3 respectively for UCHT1. A significant proportion of the resulting tetramolecular antibody complexes have dual specificity for T cells and dextran.

Magnetic Labelling of Cells

Leukapheresis collections of normal human peripheral blood were washed with PBS and either resuspended to the original volume in Hank's buffered saline plus 2% (v/v) fetal calf serum (experiments using UCHT1) or the mononuclear cells were isolated using Ficoll Hypaque density separation as described by Wognum et al. (Wognum et al., Cytometry (1987), 8: 366–371). The mononuclear cells were suspended ($2\times10^7$ cells/ml) in Hank's buffered saline plus 2% fetal calf serum (HF). The leukapheresis suspensions were approximately $2\times10^7$ cells/ml with a packed red blood cell volume of 20% (v/v).

$CD3^+$ cells in the peripheral blood leukapheresis suspensions were magnetically labelled by incubating the cell suspension with anti-dextran X anti-CD3 tetrameric antibody complexes (3 μg UCHT1/ml) on ice for 20 min. Magnetic colloidal dextran iron (final $OD_{450}$=0.2) was then added to the suspension which was mixed and incubated for another 30 min. This "start" suspension was then separated directly using HGMS (see below).

Peripheral blood mononuclear cells were incubated with anti-CD8 X anti-dextran tetrameric antibody complexes (0.5 μg OKT5/ml) on ice for 30 min. After one wash the cells were again resuspended at $2\times10^7$ cells/ml (HF) and mixed with magnetic colloidal dextran iron (final $OD_{450}$=0.1) and incubated on ice for 30 min. $CD8^+$ were then separated from this labelled cell suspension using HGMS (see below).

Heparinized whole blood was diluted 1:1 with 0.9% NaCl (USP saline) and labelled with anti-dextran X anti-CD3 tetrameric antibody complexes and colloidal dextran iron as described above.

A buffy coat suspension was prepared of whole bone marrow. The cells were diluted with a sufficient volume of USP saline to obtain a packed red blood cell volume of 20%. Cells were labelled with anti-dextran X anti-CD3 tetrameric antibody complexes and colloidal dextran iron as described above.

HGMS Filter Construction

Cylindrical filters were assembled using alternating layers of magnetic stainless steel wire mesh (430 ss, 80 mesh, 0.0055" wire, 0.0070" openings, Separator Engineering, Pointe Claire, Que., Canada) and non-magnetic stainless steel wire mesh (304 ss, 16 mesh, 0.018" wire, 0.045" openings, Western Canadian Screen, New Westminster, B.C., Canada). In initial separations 1.125" discs were cut from the mesh and stacked (alternating magnetic and non-magnetic) in a non-magnetic (316 ss) stainless steel tube (1.125" ID) with conical (90 degree apex) end pieces. It was later found that a small percentage of the cells would flow around the edges of the screen discs inside this stainless steel housing. This problem has not been recognized by numerous other workers in this field, and it is believed that reports of relatively modest depletion using HGMS techniques may partly be explained by this effect. To solve this problem several types of heat shrink tubing were explored, and the problem was solved by encasing the stack of screens and conical end pieces in two layers of medical grade heat-shrink tubing (FEP roll cover, Zeus Industrial Products Inc., Orangeburg, S.C.). A detailed diagram of the HGMS filters is shown in FIG. 1. Grooves were cut around the circumference of the end pieces to facilitate forming a seal with the shrink tubing. To shrink each layer of shrink tubing, the tubing was heated for fifteen minutes in a 250° C. oven. The end pieces and stack of mesh discs were held together during this time with a standard C-clamp. Shrink tubing filters were made in various sizes (0.5". 1,125". 1.25". 1.5" and 2.0" diameters) and lengths (5–60 layers of non-magnetic and magnetic screen or 10–120 screens in total). The end pieces were connected to standard medical tubing and blood bags via a 10–32 standard thread to Luerlock connector (Popper and Sons Inc., New Hyde Park, N.Y.).

Figure 4A:
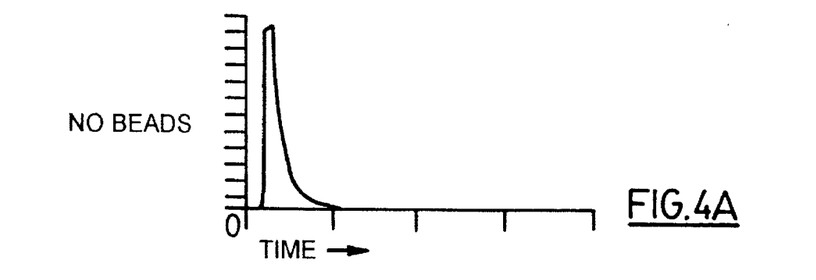
FIG. 4 shows the flow distribution achieved by different sizes of glass beads.
Figure 4B:
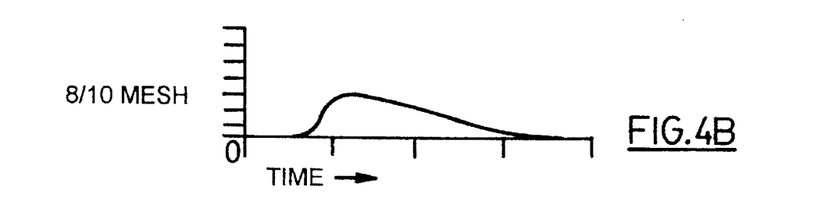
Figure 4C:
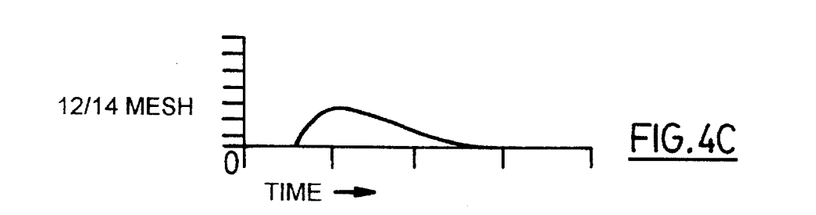
Figure 4D:
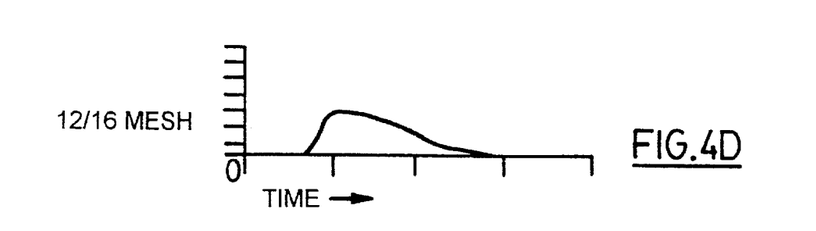
Figures 4E, 4F:
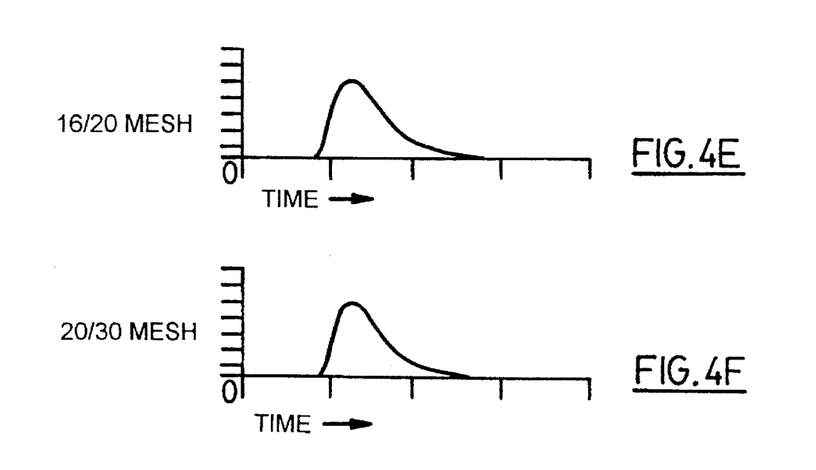

The advantages of some sort of flow distributor became evident in a 2" diameter model filter made with clear plexiglass end pieces, 120 degree cones and a single magnetic screen. With this system it was observed that at flow rates that were calculated to give an effective flow rate of 1 cm/minute at the wires of the magnetic screen, red cells or an indicator dye raced through the middle of the filter at a very high flow rate. Only a very small area of the available screen was used and at a much higher than calculated flow rate under these circumstances (FIG. 4A). After numerous failures to solve this problem by various means, a relatively simple solution was found in that insertion of glass beads between 200 and 1000 µm in diameter on top and below the mesh, resulted in an even and predictable flow pattern at the site of the magnetic mesh at the cross-section of the filter (FIGS. 4E and F). In subsequent experiments glass beads (16–20 mesh, Potters Industries Inc., Brownwood, Tex.) were loaded into the top cone (approx. ¾ of the volume of the cone) to act as a simple flow distributor.

Solenoid Magnet

The configuration for a High Gradient Magnetic Separation in the present invention has the fluid flow, gravity and the external magnetic field in the same direction and the wires perpendicular to this. To achieve this with long (40 layers plus end pieces=4 inches) 2" diameter filters a solenoid electromagnet with a 3" diameter bore was designed by A. J. Otter (Eng.) TRIUMF (Vancouver, B.C. Canada). The magnetic field in the 3" bore is 0.5 Tesla and extends for 6" vertically. This magnet is water cooled and requires a 4.5 KW power supply.

Cell Separations

Medium and cell suspensions were passed through the HGMS filters using a peristaltic pump. The dry filters were primed bottom to top at a slow flow rate of approximately 1 cm/min. Care was taken to remove all bubbles that might affect the pattern of fluid flow in the filter. After reversal of the flow direction, five column volumes of medium were passed through the filter before passage of the labelled cell suspension. As the cells were passed through the filter (at flow rates ranging from 1.0–2.0 cm/min.), the magnetic field was maintained at 0.5 Tesla and the non-magnetic cells were collected in the Flow Through fraction. The filter was washed with 3 column volumes of medium (HF) with the magnetic field on. After this the magnetic field was reduced to zero and the magnetic cells were washed off the filter. The magnetic cells were typically recovered in 3 column volumes.

Flow Cytometry

Start, flow through and purified cell suspensions were stained with FITC-conjugated F(ab')$_2$ fragments of sheep anti-mouse IgG (SAM-FITC, Cappell Cat. -No. 1311–1744) to detect the presence of antibody labelled cells in these suspensions. Cells ($10^6$) were suspended in 100 µl of SAM-FITC diluted 1:100 in staining buffer and incubated for 30 min. on ice, then washed and resuspended. Stained and unstained samples were analyzed by flow cytometry using a FACScan (Becton Dickinson, San Jose, Calif.) flow cytometer. Cells labelled with antibodies were quantitated in the Start, Flow Through and Purified fractions. The % depletion=(# of positive cells in the flow through ÷# of positive cells in the start)×100. % recovery of negative (non-target cells)=(# of negative cells in the flow through ÷# of negative cells in the start)×100.

Magnetic Matrix in HGMS Filter

Five separations were run selecting CD8$^+$ cells from peripheral blood mononuclear cells. In four separations 23 screens were stacked in the stainless steel tube described above. The order and number of screens was as follows: A) 23 magnetic screens; B) alternating magnetic and non-magnetic screens with a non-magnetic spacer at each end; C) one non-magnetic screen then alternating three layers of magnetic and non-magnetic screens at the top then 15 non-magnetic screens; D) 3 magnetic screens spaced apart with non-magnetic screens to the top, middle and bottom of the chamber (FIG. 2). All four filters were 1.125" in diameter and 0.5" long excluding end pieces. The fifth separation was with a knit mesh filter (430 ss, 50 µm diameter wire, in a plastic cylinder, 21 mm diameter and 27 mm in length) as described by Thomas et al. (Thomas et al., Hematotherapy (1993) 2: 297). A total of $4\times10^7$ mononuclear cells were passed through the filters at a flow rate of 1 cm/min. It was previously determined that 10 layers of magnetic mesh could bind 10 times this number of cells, indicating that the available surface for magnetic capture was by no means saturated in these experiments. The performance of each filter was evaluated by its ability to capture magnetically labelled CD8$^+$ cells (% depletion of CD8$^+$ cells). The results of this experiment showed that the highest efficiency of capture was achieved with 10 alternating layers of magnetic and non-magnetic screens (filter B). This array out performed twice the number of magnetic screens without spacers (non-magnetic screens) suggesting that the fields of magnetic attraction around the wires interfere with each other if the layers are not spaced. Three layers of screens at the top of the filter proved less efficient than three magnetic screens spaced one at the top, middle and bottom of the filter. This could be explained by an uneven flow distribution at the top of the filter (see below). For all subsequent experiments, alternate layers of 430 ss mesh and non-magnetic ss mesh were used.

Efficiency of Magnetic Capture in HGMS Filters

Figure 3A:
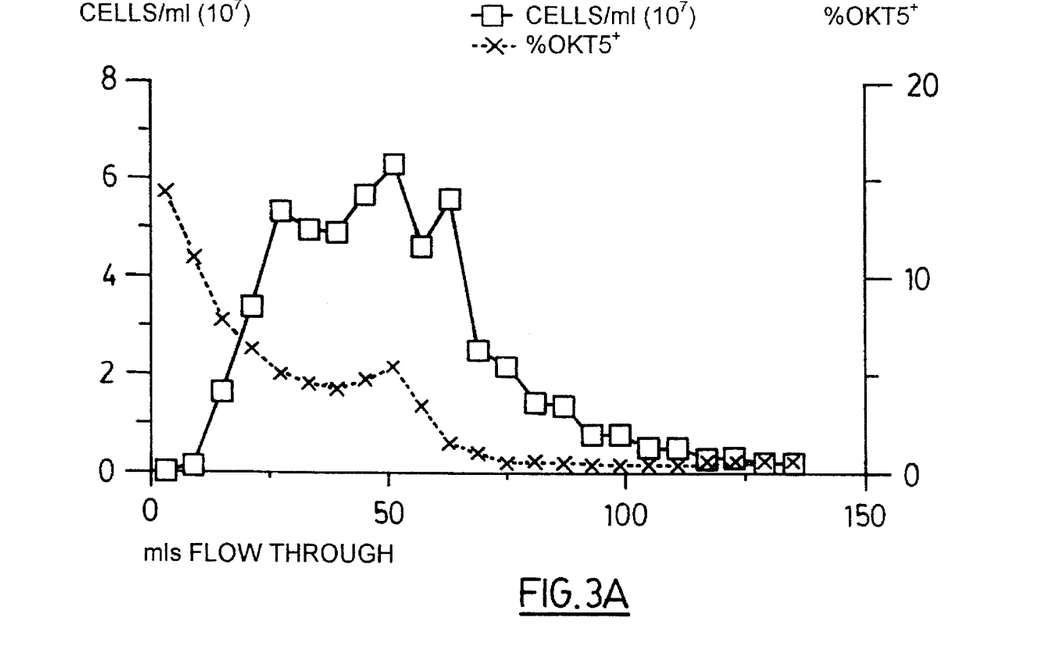
FIG. 3A is a profile of magnetic cell separation of $CD8^+$ cells using alternating magnetic and non-magnetic screens.
Figure 3B:
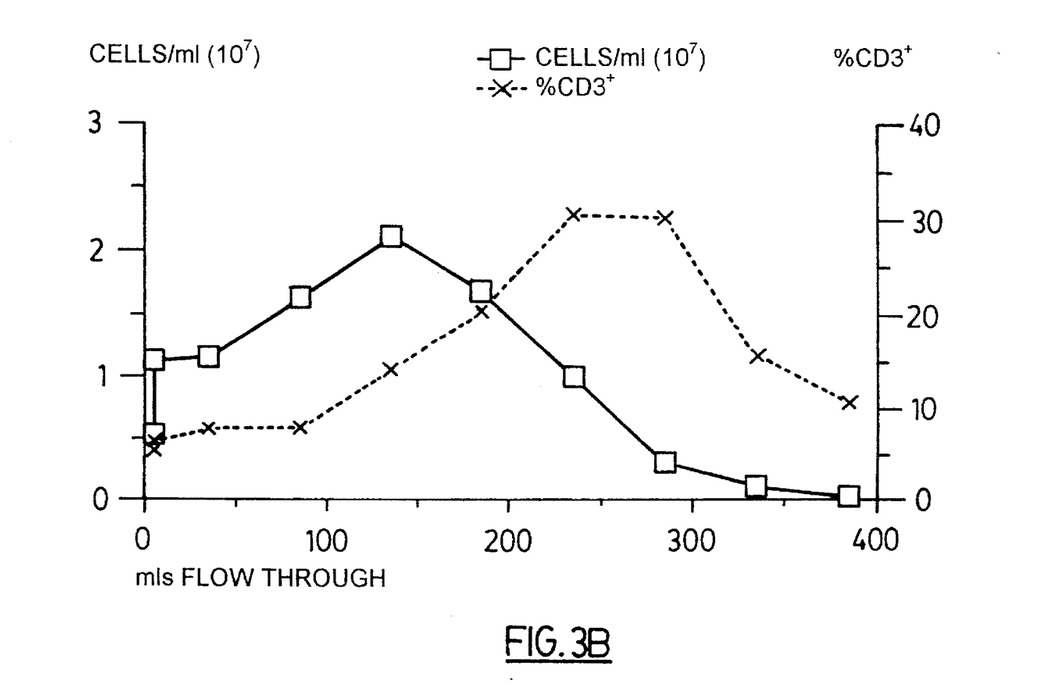
FIG. 3B is a profile of magnetic cell separation of $CD3^+$ cells using alternating magnetic and non-magnetic screens which are sealed to the housing using heat shrink material.

Twenty alternating layers of magnetic and non-magnetic screens (1.124" diameter, 40 screens in total) were stacked in the stainless steel housing tube and used to separate CD8$^+$ cells (OKT5 labelling see above) from $4.8\times10^9$ peripheral blood mononuclear cells (18.7% CD8$^+$). The start volume was 50 ml. Fractions (6 ml) of the flow through were collected. The total number of cells and the % OKT5$^+$ cells were determined for each fraction. The first two fractions collected had a CD8$^+$ cell content very similar to unseparated cells, suggesting that these first cells to come through had missed the magnetic matrix entirely (FIG. 3A). Later observations of red blood cells passing through a filter housed in a clear tube confirmed that some cells were passing around the edges of the screens avoiding close contact with the magnetic matrix. Based on these observations, the design of the filter housing was modified in order to by-pass this phenomenon. It was conceived that a close contact between the filter matrix and the filter walls could be ensured by using heat shrink tubing as a material for the filter wall. Suitable material was identified (FEP roll cover, Zeus Inc., Orangeburg, S.C.) and used to assemble HGMS filters. An example of an experiment showing that with such heat-shrink tubing the by-pass phenomena described above is avoided is illustrated in FIG. 3B. In this experiment, a time course study was done with a 20 layer 1.125" diameter sealed shrink tubing HGMS filter. Peripheral blood leukapheresis cells ($7.2\times10^9$, 120 ml 46.6% CD3$^+$, packed red blood cell volume=20%) were labelled with anti-dextran X anti-CD3 tetrameric antibody complexes and colloidal dextran iron and passed through the filter at 1 cm/min. 10 ml fractions of the flow through were collected and the total number of cells and the % $CD3^+$ determined. The first few fractions were just as efficiently depleted of $CD3^+$ cells as subsequent fractions indicating that sealing the edges of the screens to the housing had effectively prevented cells from by-passing the magnetic matrix. In this experiment, the filter was swamped with magnetic cells resulting in a decrease in the efficiency of magnetic capture after binding $5-7 \times 10^8$ cells.

Table 1 summarizes the log depletion of T cells and the % recovery of negative cells during four HGMS cell separations. All filters were composed of alternating layers of magnetic and non-magnetic 1.125" screens and were run a 1 cm/min. Two separations used an unsealed filter in a stainless steel housing (Expt. 1) and the other two used sealed shrink tubing filters (Expt. 2+3). Duplicate separations with identical cell suspensions were performed in the first two experiments. The separations with unsealed filters selected labelled $CD8^+$ cells from peripheral blood mononuclear cells ($7.2 \times 10^7$ per separation). Magnetically labelled $CD3^+$ cells (UCHT1) were used to test the sealed filters. In the first instance (Expt. 2) leukapheresis collections ($115 \times 10^7$ cells, packed red cell volume=18%) were directly labelled and separated and in the second (Expt. 3) mononuclear cells ($37 \times 10^7$ cells) were used. In view of these results, suitable heat-shrink tubing was used for the construction of HGMS filters in all subsequent cell separation experiments.

Effect of Flow Distribution on Separation Efficiency

Transparent perspex end pieces with a 90° cone were used to study the distribution of red blood cells or an indicator dye upon entry into a 2" HGMS filter. Initial studies were conducted with a mock HGMS filter containing no matrix elements at a flow rate of 8 ml/min. At a selected time point 0.5 ml of either an indicator dye (Trypan Blue 1%) or a suspension of red blood cells were injected and the absorbance at 280 nm of the column effluent was monitored. Results with the indicator dye or red blood cells were identical and are summarized in FIG. 4. Without beads the fluid did not distribute over the entire 2 inch surface of the mock HGMS filter but rapidly passed through the center, appearing in the exit long before the time required to flush the entire filter volume (FIG. 4A). In this situation the effective flow rate in the filter is many times higher than planned and only a fraction of the magnetic matrix is effectively used. Both these factors will contribute to poor depletion of labelled cells. The experiment was repeated with beads ranging from 8/10 mesh (B), 12/14 mesh (C), 12/16 mesh (D), 16/20 mesh (E) and 20/30 mesh (F). Optimum flow distribution was indicated by cells exiting in a smooth curve over the same time required to flush the void volume of the filter. 16/20 mesh beads (700–1000 μm diameter) were the largest beads still achieving satisfactory flow distribution and were chosen for subsequent experiments in order to keep the available surface area for non-specific entrapment of cells to a minimum.

A direct comparison of the efficiency of magnetic cell separation using end pieces with and without glass beads to distribute flow in the top of the filter was made in two large scale $CD3^+$ separations of peripheral blood leukapheresis cells (Table 2). The first experiment ($12.0 \times 10^8$ cells) used a 40 layer sealed filter and the second ($17.2 \times 10^8$ cells) a 60 layer sealed filter. Both experiments compared a separation with a standard heat shrink tubing filter (2" diameter) to the same filter with the top cone (part of the end piece) filled with 16/20 glass beads (to approx. ¾ volume of the entry cone). The flow rate in all separations was 1.5 cm/min. In both experiments the glass beads substantially improved the % depletion of positive cells with little or no loss of negative cells (Table 2).

EXAMPLE 2

Separation of Whole Blood

A 17 layer 1.25" diameter sealed filter with 16/20 glass beads in the top cone as described in example 1 was used to separate $CD3^+$ cells from 10 ml of whole blood ($5.4 \times 10^7$ nucleated cells, packed red cell volume of 50%). Two separations were run one with undiluted blood and the second with the 10 mls of blood diluted to 50 ml. One of the filters was coated with silicon by passage of 10 ml Methyl Hydrogen Polysiloxane (Dow Corning 1107 Fluid) at 1% (v/v) in acetone through a pre-assembled filter, followed by air (>100 ml) and further drying/heat curing for 1–2 hrs. at 80° C. The HGMS system efficiently separated undiluted and diluted (5×) whole blood (See Table 3). This finding is important because it indicates that the cell fractionation techniques that typically precedes immunomagnetic separation (i.e. Ficoll Hypaque or other forms of density separation) and which invariably result in loss of time and cells may be avoided using the HGMS filters and methods described herein. The very good recovery of cells with this method could be very useful for the purification or pre-enrichment of rare cells from peripheral blood or bone marrow.

EXAMPLE 3

Large Scale Separations

The High Gradient Magnetic Cell Separation technique as described in example 1 was scaled up to deal with the numbers of cells required in an allogeneic bone marrow transplant. An average graft ($2 \times 10^{10}$ nucleated cells total) typically contains approximately 10% or $2 \times 10^9$ T-cells. To accommodate this number of cells a 2" diameter 40 layer (80 screens total) sealed filter was assembled. This filter was connected by two three-way valves to several blood bags containing the cells, wash medium, or empty bags for the collection of flow through and purified cell fractions. The cell labelling was performed in a blood bag by injection of the anti-dextran ×anti-CD3 tetrameric antibody complexes to the bone marrow cell suspension (150 ml buffy coat cells) followed by a 30 min. incubation on ice and addition of colloidal dextran iron and a further 30 min. incubation. The results of 9 separations of peripheral blood leukapheresis cells and one bone marrow separation are presented in Table 4. All separations were run at 1 cm/minute. These results show that the HGMS device and methods described here as well as the cell suspensions that can be generated with this device and methods are readily adapted to clinical scale separations. The high degree of target cell depletion required in clinical T-cell depletions with excellent (i.e. >50%) recovery of hematopoietic progenitor cells described here is novel and should prevent or attenuate GVHD and result in rapid engraftment.

EXAMPLE 4

Depletion of $CD3^+$ T cells from Allogeneic Bone Marrow Using the Device of the Invention The usefulness of the device for the depletion of T cells from allogeneic bone marrow transplants is illustrated in the laboratory results of eight clinical T cell depletion procedures (Table 5). For these separations, a buffy coat fraction (~150 ml) of the bone marrow suspensions (~1.5 l) was prepared on a COBE 2991 cell centrifuge. This suspension was diluted with saline to set the packed red blood cell volume at approximately 15% (~300 ml total volume). UCHT1 (mouse $IgG_1$-anti-CD3)× DX-1 (mouse $IgG_1$-anti-dextran)×P9 (F(ab')$_2$(rat anti-mouse $IgG_1$) tetrameric complexes (at a 1:2:3 molar ratio of respectively UCHT1, DX1 and P9 F(ab')$_2$ antibodies) were added to give a final concentration of 3 µg/ml UCHT1, after a 30 minute incubation period on ice, magnetic iron dextran particles were added to a final $OD_{450}$ of the particles of 0.2 AUFS and incubation on ice was continued for another 30 minutes. The cells were then passed through a 2" magnetic filter (as described in Example 1) positioned in a 0.5 T vertical magnetic field containing, 40–60 layers of magnetic screens at the indicated flow rate using a peristaltic pump. Details of the magnetic filter device used for these studies are provided in Example 1. The cells that were recovered in the flow through (depleted of $CD3^+$ cells) as well as samples of the cells prior to magnetic separation were assayed for their content of CD3 and $CD34^+$ cells using flow cytometry as described in Example 1. The results of the eight clinical T cell depletion procedures are shown in Table 5. As shown in the Table, the method of the present invention depleted CD3+ cells at a good efficiency (>2 log depletion) while recovering >50% of the CD34+ cells.

EXAMPLE 5

Removal of CD45RA+ Lymphoma Cells from Bone Marrow

This example illustrates an improved method for removing lymphoma cells from bone marrow or blood. Table 6 shows that immunomagnetic removal of cells that express CD45RA using the methods and device described herein results in highly efficient (>4 log) removal of spiked Daudi lymphoma cells from either peripheral blood or bone marrow cells without significant loss (<40% of start material) of the cells that do not express CD45RA. The recovery of colony-forming cells that do not express CD45RA (BFU-e) was also >60% in these experiments.

In the experiments, $CD45RA^+$ lymphoma cells (Daudi, cell line cells) were labelled with FITC and mixed with peripheral blood or bone marrow cells at the indicated percentage. The cells were then incubated with 8d2 (mouse $IgG_1$-anti-CD45RA)×DX1 (mouse $IgG_1$-anti-dextran)×P9 F'(ab)2 (rat anti-mouse $IgG_1$) tetrameric antibody complexes at 0.5 µg/ml of 8d2. The labelled cell suspensions were then passed through a 0.5 inch, 40 layer filter at 1 cm/minute. A total of three experiments were performed that illustrated the unique advantages of the method of the invention. The results of these experiments are shown in Table 6. For removal of lymphoma cells from clinical autologous peripheral blood or bone marrow grafts, a combination of antibodies specific for different cell surface antigens on lymphoma cells such as CD10, CD19 and CD20 can be used to minimize the chance that variant lymphoma cells would escape magnetic capture.

EXAMPLE 6

Purging of breast cancer cells from peripheral blood and bone marrow.

Autologous transplantation of peripheral blood stem cells (PBSC) or bone marrow is increasingly used in the treatment of poor prognosis breast cancer patients. A concern in such transplant procedures is the possible contamination of tumour cells in the autologous graft. To examine the efficiency of the device/filter and methods disclosed herein for the immunomagnetic removal of breast cancer cells, tumour cells from breast carcinoma cell line BT20 (ATCC) were labelled with fluorescein in order to allow rapid and sensitive detection among unlabelled normal peripheral blood and bone marrow cells. The cell mixture was then labelled with tetrameric antibody complexes containing mouse $IgG_1$ anti-breast carcinoma antibody H23, mouse $IgG_1$, anti-dextran DX1 and F(ab')$_2$ fragments of rat anti-mouse $IgG_1$ P9 at a 1:2:3 molar ratio, at 3 µg/ml of H23. After 15 minutes at 4° C., magnetic iron-dextran was added to the cell suspension to give an $OD_{450}$ of these particles of 0.2 AUFS and incubation was continued for another 30 minutes prior to passage over 0.5 inch filters containing 40 layers of magnetic screens at a flow rate of 0.5 cm/min. The cells in the flow through as well as the cells prior to magnetic labelling were counted and analyzed by flow cytometry to generate the data shown in Table 7.

The results of these experiments clearly indicate that even with a single antibody highly efficient (>3 log) removal of breast cancer cells can be obtained with the methods disclosed herein and that application of this method allows recovery of the majority of $H23^-$, $CD34^+$ cells. Clinical applications as described for $CD3^+$ T cells would probably use multiple antibodies with specificity for different antigens expressed on breast cancer cells.

EXAMPLE 7

Purification of $CD34^+$ cells by immunomagnetic removal of $CD34^-$ cells.

This example illustrates the results of an experiment in which a single step immunomagnetic purification of $CD34^+$ $CD38^-$ cells was performed with three different bone marrow cell suspensions (Table 8). In this experiment, a mixture of tetrameric antibody complexes with dual specificity for dextran and respectively glycophorin (10F7MN, 1 µg/ml), CD45RA (8d2, 1 µg/ml), CD67 (B13 29, 5 µg/ml), CD3 (UCHT1, 3 µg/ml) and an undefined platelet antigen (3H2, 5 µg/ml) was added to the bone marrow cells (1–3×10$^7$ cells/ml). After a 15 minute incubation at 4° C., iron-dextran complexes were added to the cells (to an $OD_{450}$ of the magnetic particles of 0.2 AUFS) and incubation was continued for another 30 minutes. The cells were then passed over a 0.5 inch diameter magnetic filter containing 40 layers of magnetic mesh at a flow rate of 1 cm/min. The cells that did not bind to the filter (flow through) as well as cells prior to magnetic labelling were counted and analyzed by flow cytometry. The results of this experiment are shown in Table 8. Note that the purity of $CD34^+$ cells in this experiment was comparable to that obtained by the immunoadsorption technique mentioned above and yet the majority of $CD34^+$ $CD38^{low}$ cells were recovered without modifications or antibody at their surface.

EXAMPLE 8

Depletion of murine cells that express lineage markers.

Figure 5A:
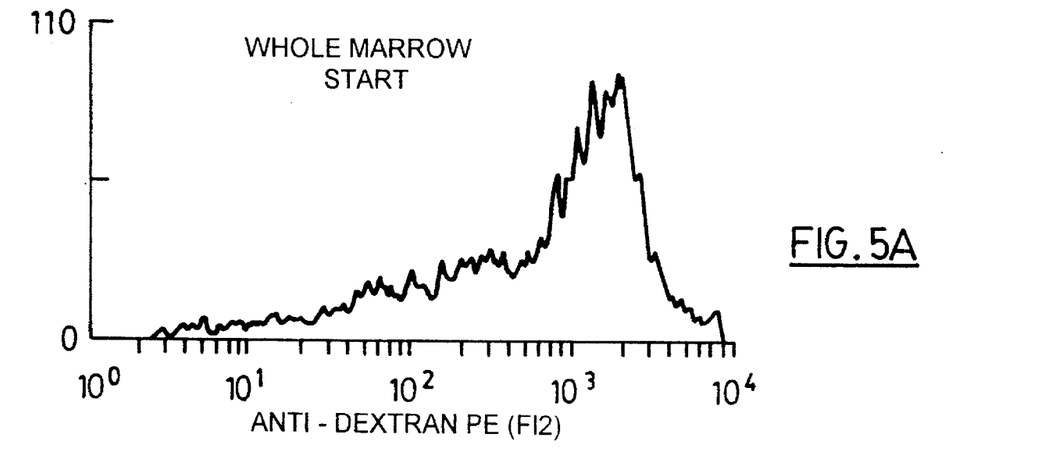
FIG. 5 are graphs showing the indirect immunomagnetic removal of lineage positive hematopoietic cells from murine bone marrow using anti-biotin x anti-dextran complexes.
Figure 5B:
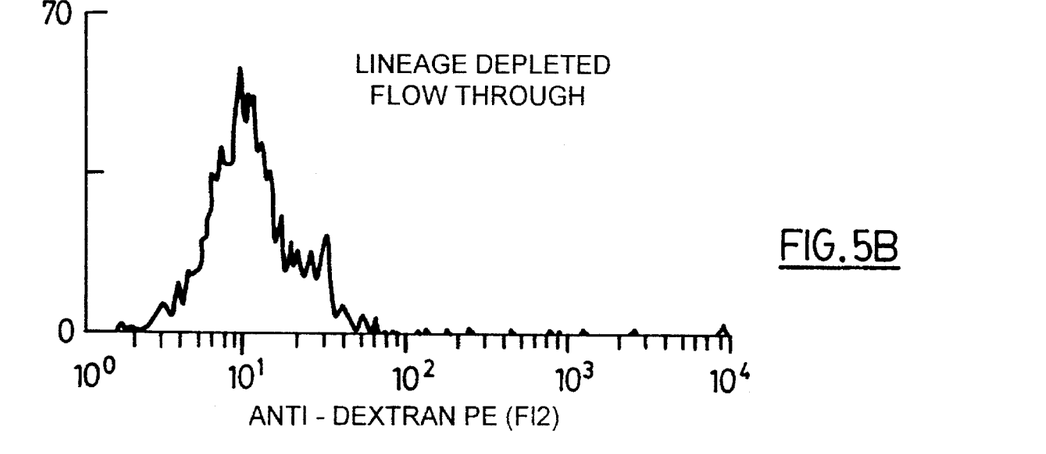

Murine hematopoietic stem cells can be enriched from bone marrow by removal of cells that express markers which correspond to a particular differentiation lineage (Spangrude and Scollay, Exp. Hematol. 18: 920–926, 1990). Indirect immunomagnetic removal of lineage positive cells from murine bone marrow using anti-biotin×anti-dextran complexes is shown in FIG. 5. Mouse bone marrow cells were labelled with a cocktail of five biotinylated monoclonal antibodies with specificity for different lineage-specific antigens as described by Spangrude and Scollay (supra). After a wash step the cells were incubated with anti-biotin×anti-dextran tetrameric antibody complexes followed by magnetic dextran-iron ($O.D._{450}=0.2$). The cells were passed through a 40 layer 0.5" diameter filter (described in example 1) at a flow rate of 1 cm/min. For analysis cells were stained with anti-dextran antibodies conjugated to R-Phycoerythrin. FIG. 5 illustrates the efficient removal of lineage positive cells. This separation of murine bone marrow resulted in a 10-fold enrichment of lineage negative cells including candidate hematopoietic stem cells with a $Sca^+Lin^-Rh123^{dull}$ phenotype and approximately 75% recovery of lineage negative cells. No inhibitory effects on in vitro colony-formation or in vivo repopulation by the separation procedure were observed. This experiment illustrates that rapid depletion of lineage positive cells can be achieved using the method and device disclosed herein.

EXAMPLE 9

Immunomagnetic removal of red blood cells.

Approximately half of the volume of normal peripheral blood consists of mature red blood cells. Typically these cells exceed nucleated cells by >100 fold. For many clinical as well as research applications, removal of red blood cells is required or desirable and such red blood cell depletion can be achieved using a variety of techniques. One of the most common ways to remove red blood cells from peripheral blood or bone marrow is by means of Ficoll Hypaque density centrifugation. This example illustrates the immunomagnetic removal of erythrocytes using a single antibody with specificity for glycophorin (10F7MN). As shown in Table 9, the method of the invention resulted in efficient depletion (>3 log) of red blood cells and recovers most (>50%) of the nucleated cells (Table 9). In contrast, the more laborious Ficoll procedure results in a much poorer recovery of nucleated cells. Because the immunomagnetic procedure disclosed here does not involve any wash steps, it is very suitable for automation.

While what is shown and described herein constitutes various preferred embodiments of the device and method subject invention, it will be understood that various changes can be made to such embodiments without departing from the subject invention, the scope of which is defined in the appended claims.

TABLE 1

Depletion of T-cell from peripheral blood using High Gradient Magnetic Separation. Duplicate separations with identical cell suspensions were performed in Expt. 1 and 2. In Expts. 2 and 3, the edges of the wire matrix were embedded in the filter housing (heat shrink tubing).

| Expt. # | # of Layers | Log Depletion of T-Cells | % Recovery of Negative Cells |
|---------|-------------|--------------------------|------------------------------|
| 1       | 10          | 0.64/0.54                | 78/90                        |
|         | 20          | 1.05/1.05                | 60/65                        |
| 2       | 15          | 2.55/2.44                | 88/72                        |
| 3       | 15          | 3.05                     | 73                           |

TABLE 2

Comparison of large scale HGMS T-cell depletions with or without glass beads to distribute flow in the top of the filter. $CD3^+$ cells were depleted from peripheral blood leukapheresis cells.

|  | Log Depletion $CD3^+$ Cells | % Recovery Negative Cells |
|---|---|---|
| Expt. 1 40 layers of screen | | |
| without glass beads | 1.9 | 58 |
| with glass beads | 2.4 | 53 |
| Expt. 2 60 layers of screen | | |
| without glass beads | 2.5 | 54 |
| with glass beads | 3.5 | 64 |

TABLE 3

Depletion of $CD3^+$ cells from whole blood. In Expt. 1, 10 mls of blood was separated undiluted on a siliconized HGMS filter. In Expt. 2, 10 mls of blood was diluted to 50 mls prior to passage through a non-siliconized filter.

|  | % Depletion $CD3^+$ Cells | Log Depletion $CD3^+$ Cells | Log Depletion Red Blood Cells | % Recovery Negative Cells | % Recovery $CD3^+$ Cells | Fold Enrichment $CD3^+$ Cells |
|---|---|---|---|---|---|---|
| Expt. 1 | 95.4 | 1.33 | 2.69 | 57 | 61 | 4.4 |
| Expt. 2 | 99.6 | 2.40 | 2.81 | 44 | 53 | 4.2 |

TABLE 4

Large scale separations of CD3+ cells using High Gradient Magnetic Separation.

| Expt. # | CD3+ Cells $10^8$ | Log Depletion of CD3+ Cells | % Recovery of Negative Cells |
|---|---|---|---|
| Peripheral Blood (Leukapheresis Collection) | | | |
| 1 | 8.6 | 2.90 | 71 |
| 2 | 8.6 | 3.50 | 71 |
| 3 | 9.9 | 3.22 | 58 |
| 4 | 20.6 | 2.00 | 70 |
| 5 | 5.7 | 2.46 | 82 |
| 6 | 20.1 | 2.10 | 93 |
| 7 | 8.8 | 3.20 | 88 |
| 8 | 17.8 | 2.57 | 89 |
| 9 | 16.5 | 2.64 | 100 |
| Percolled Bone Marrow | | | |
| 1 | 6.2 | 2.75 | 68* |

* % recovery of CD34+ cells was 84% and the recovery of hemopoietic colony forming cells was 126%.

TABLE 5

Removal to CD3+ T-cells from clinical bone marrow grafts from matched unrelated donors.

| Patient # TCDM- | Total # of Cells Processed $10^8$ | Log Depletion of CD3+ Cells | % Recovery of CD34+ Cells |
|---|---|---|---|
| 8* | 58 | 1.55 | 95 |
| 9 | 99 | 2.50 | 93 |
| 10** | 98 | >3.50 | 45 |
| 12 | 141 | >3.90 | 85 |
| 14 | 187 | 3.47 | 73 |
| 16 | 505 | 2.19 | 77 |
| 17 | 150 | >3.13 | 66 |
| 18 | 293 | >3.76 | 73 |
| Mean | 191 | >3.00 | 76 |

*Magnetic separation flow rate = 1.0 cm/min. All other separations were run at 0.5 cm/min.
**Marrow suspension was density separated using Percoll prior to magnetic separation.

TABLE 6

Purging lymphoma cells from peripheral blood and bone marrow using high gradient magnetic separation.

| Sample | Total # of Cells $10^7$ | Log Depletion of Tumor Cells (Daudi*) | % Recovery of CD45RA− Cells | % Recovery of CD34+ Cells | % Recovery of BFU-E |
|---|---|---|---|---|---|
| Peripheral Blood Leukapheresis 0.5% Daudi | 79.5 | >4.2 | 65 | ND | ND |
| Normal Bone Marrow 15.7% Daudi | 7.0 | >5.8 | 75 | 33 | 63 |
| Lymphoma Bone Marrow 7.8% Daudi | 4.4 | >6.0 | 74 | 24 | 60 |

ND = Not Done, CD34+ cells are normally extremely rare in peripheral blood making the determination of the recovery of CD34+ cells using FACS difficult.
*Daudi cells were first labelled with FITC and added to the start cell suspension. These Daudi cells were then detected in the separated fractions using FACS as described.

TABLE 7

Purging breast carcinoma cells (BT20) from peripheral blood and bone marrow using High Gradient Magnetic Separation.

| Sample | Total # of Cells 10⁷ | Log Depletion BT20 Cells | % Recovery of H23-Lymphocytes | % Recovery of CD34⁺ Cells |
|---|---|---|---|---|
| Peripheral blood Leukapheresis | 2.5 | 3.21 | 85 | ND |
| Normal Bone Marrow | 2.2 | 3.80 | 80 | 68 |

TABLE 8

Depletion of cells expressing lineage markers from human bone marrow to enrich for primitive hematopoietic progenitors (CD34⁺, CD38$^{lo}$).

| Bone Marrow Sample | Total # (10⁷) of Nucleated Cells in the Start Fraction | Start Fraction % CD34⁺ CD38$^{lo}$ | % CD34 in Flow Through Fraction | Flow Through Fraction % CD34⁺ CD38$^{lo}$ | % Recovery of CD34⁺ CD38$^{lo}$ Cells | Enrichment of CD34⁺ CD38$^{lo}$ Cells |
|---|---|---|---|---|---|---|
| Organ Donor Marrow #7 | 1.94 | 0.6 | 67.2 | 16.6 | 72 | 28x |
| Organ Donor Marrow #6 | 2.48 | 0.3 | 53.1 | 11.2 | 60 | 37x |
| Aspirated Bone Marrow | 0.56 | 0.4 | 75.0 | 21.1 | 59 | 53x |

TABLE 9

A comparison of erythrocyte removal from whole blood using High Gradient Magnetic Separation or Ficoll Density Separation.

| Technique | Log Depletion of Erythrocytes | % Recovery Nucleated Cells | % Recovery CD3* Lymphocytes |
|---|---|---|---|
| HGMS* | 3.1 | 65.7 | 79.2 |
| Ficoll | 3.9 | 21.3 | 44.8 |

*Whole blood was magnetically labelled with anti-glycophorin x anti-dextran tetrameric antibody complexes and magnetic dextran iron as described in the methods section.
Each technique processed 10 ml of whole blood with approximately 5 × 10¹¹ erythrocytes.

We claim:

1. A device for separating magnetically labelled cells in a sample using an applied magnetic field, comprising:
   (a) a housing;
   (b) an inlet element at the top portion of the housing defining an inlet chamber, which has an input end and an output end with the output end being larger than the input end;
   (c) a filter chamber adjacent to the output end of the inlet element for filtering the magnetically labelled cells from the fluid while allowing unlabelled cells to pass through when a magnetic filed is applied thereto, and containing a multiplicity of magnetic matrix elements extending transversely across the filter chamber;
   (d) an outlet element for collecting the fluid which passes through the filter chamber and defining an outlet chamber, which has an input end coupled to the filter chamber and an output end, with the input end being larger than the output end; and
   (e) flow distribution means in both the inlet and outlet chambers, for distributing the flow generally uniformly across the filter chamber and comprising spherical particles; wherein the housing is generally tubular and comprises a heat shrink material which has been heat shrunk onto the magnetic matrix elements whereby the magnetic matrix elements are embedded at their peripheries in the housing.

2. The device as defined in claim 1, wherein the inlet chamber is frusto-conical and extends between the input end and output end thereof with the output end being of greater diameter than the input end, and the outlet chamber is frusto-conical and extends between the input end and the output end thereof with the output end being of smaller diameter than the input end.

3. A device for separating magnetically labelled cells in a sample using an applied magnetic field, comprising:
   (a) a housing;
   (b) an inlet element at the top portion of the housing defining an inlet chamber, which has an input end and an output end with the output end being larger than the input end;
   (c) a filter chamber adjacent to the output end of the inlet element for filtering the magnetically labelled cells from the fluid while allowing unlabelled cells to pass through when a magnetic filed is applied thereto, and containing a multiplicity of magnetic matrix elements extending transversely across the filter chamber;
   (d) an outlet element for collecting the fluid which passes through the filter chamber and defining an outlet chamber, which has an input end coupled to the filter chamber and an output end; and
   (e) flow distribution means in both the inlet and outlet chambers, for distributing the flow generally uniformly across the filter chamber and comprising spherical particles, wherein the flow distribution means comprises particles of between 50 microns and 1 mm diameters; and wherein the housing is generally tubular and comprises a heat shrink material which has been heat shrunk onto the magnetic matrix elements whereby the magnetic matrix elements are embedded at their peripheries in the housing.

4. The device as defined in claim 3, wherein the particles are generally spherical and are one of glass beads or polyacrylamide beads.

5. The device as defined in claim 3, wherein the magnetic matrix elements are magnetic wire meshes comprising a multiplicity of interwoven magnetic wires.

6. The device as defined in claim 5, wherein the magnetic matrix elements are vertically spaced from 6 to 9 times the diameter of the magnetic wires.

7. The device as defined in claim 5, wherein there is a non-magnetic matrix element between each adjacent pair of magnetic matrix elements which are maintained spaced apart by the non-magnetic element.

8. The device defined in claim 7, wherein the non-magnetic matrix element comprises a mesh made of interwoven non-magnetic wire having a substantially greater diameter than the wire of the magnetic meshes.

9. A device as claimed in claim 3, wherein the outlet element includes an outlet mesh support at the upper end of the outlet element, for supporting and retaining the particulate material in the outlet chamber.

10. A device as claimed in claim 9, wherein the magnetic matrix elements are spaced apart to maximize the magnetic capture of magnetically labelled cells onto the magnetic matrix when subject to a magnetic field, with one magnetic matrix element being located adjacent the inlet element and another magnetic matrix element being located adjacent to the outlet element, to retain the particulate material in the inlet and outlet chambers.

11. A device as claimed in claim 10, which includes a multiplicity of non-magnetic matrix elements alternating with the magnetic matrix elements, whereby each pair of magnetic matrix elements is spaced apart by a respective non-magnetic matrix element.

12. A device as claimed in claim 11, wherein the magnetic matrix elements are generally planar and comprise interwoven magnetic wires.

13. A device as claimed in claim 12, wherein the magnetic matrix elements are spaced apart from 6 to 9 times the diameter of the magnetic wires thereof.

14. A device for separating magnetically labelled cells in a sample using an applied magnetic field, comprising:

(a) an inlet element having an output end;

(b) a filter chamber adjacent to the output end of the inlet element for filtering the magnetically labelled cells from the fluid while allowing unlabelled cells to pass through when a magnetic field is applied thereto, and containing a multiplicity of magnetic matrix elements extending transversely across the filter chamber;

(c) an outlet element for collecting the fluid which passes through the filter chamber and having an input end connected to the filter chamber; and (d) a housing which is generally tubular, which comprises a heat shrink material, and which encloses the inlet and outlet elements and the filter chamber, the material having been heat shrunk so as to retain securely the inlet and outlet elements and so that the peripheries of the magnetic matrix elements are embedded therein.

15. A device as claimed in claim 14, wherein the inlet element has an input end and defines a frusto-conical inlet chamber extending between the input end and the output end thereof with the output end being of greater diameter than the input end, and the outlet element has an output end and defines a frusto-conical outlet chamber extending between the input end and the output end thereof, with the output end being of smaller diameter than the input end, and wherein the flow distribution means comprises spherical particles of between 50µ and 1 mm diameter located in the frusto-conical inlet and outlet chambers.

16. A device as claimed in claim 15, wherein the magnetic matrix elements are magnetic wire meshes comprising a multiplicity of interwoven magnetic wires, and wherein there is a non-magnetic matrix element between each adjacent pair of magnetic matrix elements, to maintain the magnetic matrix elements spaced vertically apart, the magnetic matrix elements being spaced apart by an amount from 6 to 9 times the diameter of the magnetic wires.

17. A device for separating magnetically labelled cells in a sample using an applied magnetic field, comprising:

(a) a housing;

(b) an inlet element at the top portion of the housing having an input end and an output end;

(c) a filter chamber adjacent to the output end of the inlet element for filtering the magnetically labelled cells from the fluid while allowing unlabelled cells to pass through when a magnetic filed is applied thereto, and containing a multiplicity of magnetic matrix elements extending transversely across the filter chamber; and (d) an outlet element for collecting the fluid which passes through the filter chamber having an input end coupled to the filter chamber and an output end, wherein the magnetic matrix elements are ordered and spaced apart so as to maximize the capture of magnetically labelled materials when a magnetic filed is applied; and wherein the housing is generally tubular and comprises a heat shrink material which has been heat shrunk onto the magnetic matrix elements whereby the magnetic matrix elements are embedded at their peripheries in the housing.

18. A device as claimed in claim 17, wherein the magnetic matrix elements are magnetic wire meshes comprising a multiplicity of interwoven magnetic wires.

19. A device as claimed in claim 18, wherein the magnetic matrix elements are vertically spaced from 6 to 9 times the diameter of the magnetic wires.

20. A device as defined in claim 19, wherein there is a non-magnetic matrix element between each adjacent pair of magnetic matrix elements, to space the magnetic matrix elements.

21. A device as defined in any one of claims 18, 19 and 20, wherein the housing has been heat shrunk onto the inlet and outlet elements to securely retain the inlet and outlet elements.

* * * * *